(12) United States Patent
Stramski et al.

(10) Patent No.: US 9,645,070 B2
(45) Date of Patent: May 9, 2017

(54) NANOPARTICLE ANALYZER

(71) Applicant: The Regents of the University of California, Oakland, CA (US)

(72) Inventors: Dariusz Stramski, San Diego, CA (US); Jan J. Tatarkiewicz, San Diego, CA (US); Rick A. Reynolds, San Diego, CA (US); Monette Karr, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/730,138

(22) Filed: Jun. 3, 2015

(65) Prior Publication Data

US 2015/0346076 A1 Dec. 3, 2015

Related U.S. Application Data

(60) Provisional application No. 62/007,312, filed on Jun. 3, 2014.

(51) Int. Cl.
  *G01N 15/14* (2006.01)
  *G01N 15/02* (2006.01)
  *G01N 15/00* (2006.01)

(52) U.S. Cl.
  CPC ..... *G01N 15/1434* (2013.01); *G01N 15/0227* (2013.01); *G01N 15/1429* (2013.01); *G01N 15/1463* (2013.01); *G01N 2015/0038* (2013.01); *G01N 2015/0238* (2013.01); *G01N 2015/1493* (2013.01)

(58) Field of Classification Search
  None
  See application file for complete search history.

(56) References Cited

U.S. PATENT DOCUMENTS

| | | | |
|---|---|---|---|
| 6,366,403 B1* | 4/2002 | Kurtz | F27D 21/02 250/216 |
| 6,836,559 B2 | 12/2004 | Abdel-Fattah et al. | |
| 7,679,742 B2 | 3/2010 | Haddock et al. | |
| 2004/0057050 A1* | 3/2004 | Beck | G01N 15/1459 356/336 |

(Continued)

FOREIGN PATENT DOCUMENTS

WO WO-2013185784 A1 12/2013

*Primary Examiner* — Jason Heidemann
*Assistant Examiner* — Brian Shin
(74) *Attorney, Agent, or Firm* — Manuel de la Cerra

(57) ABSTRACT

Methods for detecting and analyzing individual nanoparticles of the same, similar, or different sizes co-existing in a fluid sample using multi-spectral analysis are disclosed. A plurality of light sources may be configured to produce a plurality of light beams at different spectral wavebands. An optical assembly may be configured to combine the plurality of light beams into one or more incident light sheets. Each incident light sheet may illuminate one or more nanoparticles in a liquid sample. One or more image detectors may be configured to detect, using a plurality of wavelengths, light scattered or emitted by one or more nanoparticles. The plurality of wavelengths may correspond to the different spectral wavebands of the plurality of light beams. Related apparatus, systems, techniques, and articles are also described.

32 Claims, 6 Drawing Sheets

(56) References Cited

U.S. PATENT DOCUMENTS

| | | | |
|---|---|---|---|
| 2007/0165225 A1* | 7/2007 | Trainer | G01N 15/0205 356/335 |
| 2008/0137080 A1 | 6/2008 | Bodzin et al. | |
| 2008/0232653 A1* | 9/2008 | Rowe | A61B 5/0059 382/124 |
| 2009/0323061 A1 | 12/2009 | Novotny et al. | |
| 2012/0046191 A1* | 2/2012 | Vu | B82Y 15/00 506/9 |
| 2012/0105600 A1* | 5/2012 | Meyer | G01N 21/49 348/50 |
| 2012/0219985 A1* | 8/2012 | Yoon | G01N 15/04 435/32 |
| 2012/0309636 A1 | 12/2012 | Gibbons et al. | |
| 2014/0099659 A1* | 4/2014 | Keller | G01N 21/6486 435/29 |

* cited by examiner

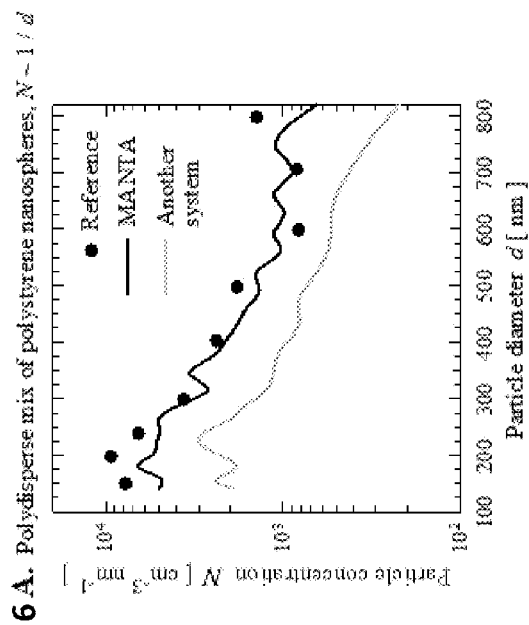
FIG. 6A. Polydisperse mix of polystyrene nanospheres, $N \sim 1/d$
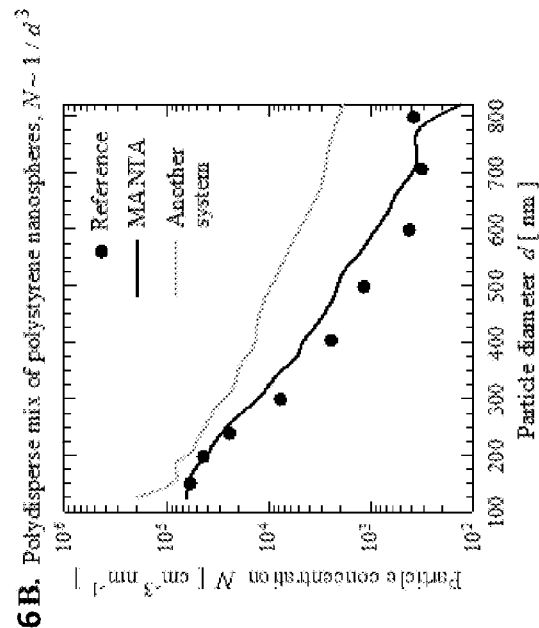
FIG. 6B. Polydisperse mix of polystyrene nanospheres, $N \sim 1/d^3$

NANOPARTICLE ANALYZER

CROSS REFERENCE TO RELATED APPLICATION

This application claims priority under 35 U.S.C. §119(e) to U.S. Provisional Patent Application No. 62/007,312, filed on Jun. 3, 2014, titled "Nanoparticle Analyzer", the disclosure of which is herein incorporated by reference in its entirety.

STATEMENT OF GOVERNMENT SPONSORED SUPPORT

This subject matter disclosed herein was made with government support under grant number OCE-11-26870 awarded by the National Science Foundation. The government has certain rights in the invention.

BACKGROUND

Nanoparticles are ubiquitous and by far the most abundant particle-like entities in natural environments on Earth and are widespread across many applications associated with human activities. There are many types of naturally occurring nanoparticles and man-made (engineered) nanoparticles. Nanoparticles occur in air, aquatic environments, rain water, drinking water, biofluids, pharmaceuticals, drug delivery and therapeutic products, and a broad range of many industrial products. Nanoparticles usually occur within polydisperse assemblages which are characterized by co-occurrence of differently sized particles.

Given the widespread usage of nanoparticles, the ability to control and accurately characterize their properties may be useful to many applications. Conventional methods for measuring nanoparticle properties may be inaccurate for polydisperse samples of mixed nanoparticle sizes, which are common in many applications. Some of these conventional approaches make measurements on an ensemble of a large number of nanoparticles within a sample. Because the light scattered from all nanoparticles is measured simultaneously, it may be difficult to resolve the nanoparticles into their constituent sizes when there is a range of particle sizes. Other approaches fail to account for the large differences in the intensity of scattered light produced by differently sized nanoparticles across the range of nanoparticle sizes. In these approaches, the low scattering signals from small nanoparticles may be undetected, or the high scattering signals from larger nanoparticles can obscure the signals from smaller nanoparticles. As a result of these deficiencies, the concentration of nanoparticles of any given size, and hence the entire size distribution, can be subject to unknown error.

SUMMARY

In some example implementations, there may be provided systems, methods, and articles of manufacture for detecting and analyzing individual nanoparticles of the same, similar, or different sizes co-existing in a fluid sample using multi-spectral analysis.

In one aspect, a plurality of light sources are configured to produce a plurality of light beams at different spectral wavebands. An optical assembly is configured to combine the plurality of light beams into one or more incident light sheets. Each incident light sheet illuminates one or more nanoparticles in a liquid sample. One or more image detectors are configured to detect, using a plurality of wavelengths, light scattered by one or more nanoparticles. The plurality of wavelengths correspond to the different spectral wavebands of the plurality of light beams.

The above methods, apparatus, and systems may, in some implementations, further include one or more of the following features.

A recording device may be configured to record a sequence of images obtained from the one or more image detectors in one or more movies.

At least one processor may be configured to at least detect and track a movement of the one or more nanoparticles based on at least two images from the sequence of images. The at least two images may display a scattering of the one or more incident light sheets by the one or more nanoparticles. The at least one processor may also be configured to determine a particle size distribution of the one or more nanoparticles from the one or more movies. The particle size distribution may include one or more concentration values for one or more nanoparticle diameters.

The detect and track may include one or more of the following: splitting the one or more movies into one or more separate spectral components to generate one or more spectral images and backfilling each spectral image; eliminating one or more false features from the one or more movies, the eliminating based on one or more criteria including an intensity threshold or a size threshold; tracking only a subset of the one or more nanoparticles that are present in one or more pre-selected starting frames of the one or more movies; eliminating drift motion of the one or more nanoparticles; or eliminating duplicate nanoparticle tracks from the one or more spectral components of the one or more movies.

The one or more nanoparticles may be moving.

The one or more nanoparticles may not be moving.

Each light beam may be output at a separately adjustable power level.

The optical assembly may include one or more of a mirror, a beam combiner, a slit, a cylindrical lens, or a long working distance objective.

The plurality of light beams may be a part of a visible light spectrum.

The plurality of light beams may include light beams having a blue spectral waveband, a green spectral waveband, and a red spectral waveband.

The one or more image detectors may include a Bayer pattern filter configured to separately detect the different spectral wavebands of the plurality of light beams.

The one or more image detectors may include a Bayer pattern filter configured to produce one or more Bayer pattern images having separate color pixels.

The optical assembly may further include a polarizer arranged between the plurality of light sources and the liquid sample. The polarizer may be configured to vertically polarize the plurality of light beams relative to a scattering plane in order to optimize illumination of the liquid sample relative to a thermal energy transferred to the liquid sample from the one or more incident light sheets.

The one or more image detectors may be further configured to detect, at the plurality of wavelengths, the light scattered by the one or more nanoparticles simultaneously.

The one or more image detectors may be further configured to at least detect light produced by fluorescence and/or other radiation emitted by the one or more nanoparticles.

It is to be understood that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

DESCRIPTION OF THE DRAWINGS

The accompanying drawings, which are incorporated in and constitute a part of this specification, show certain aspects of the subject matter disclosed herein and, together with the description, help explain some of the principles associated with the subject matter disclosed herein. In the drawings.

FIGS. 6A and 6B illustrate plots of laboratory results conducted with a polydisperse mix of nanosphere size standards, in accordance with some example implementations.

Figure 1:
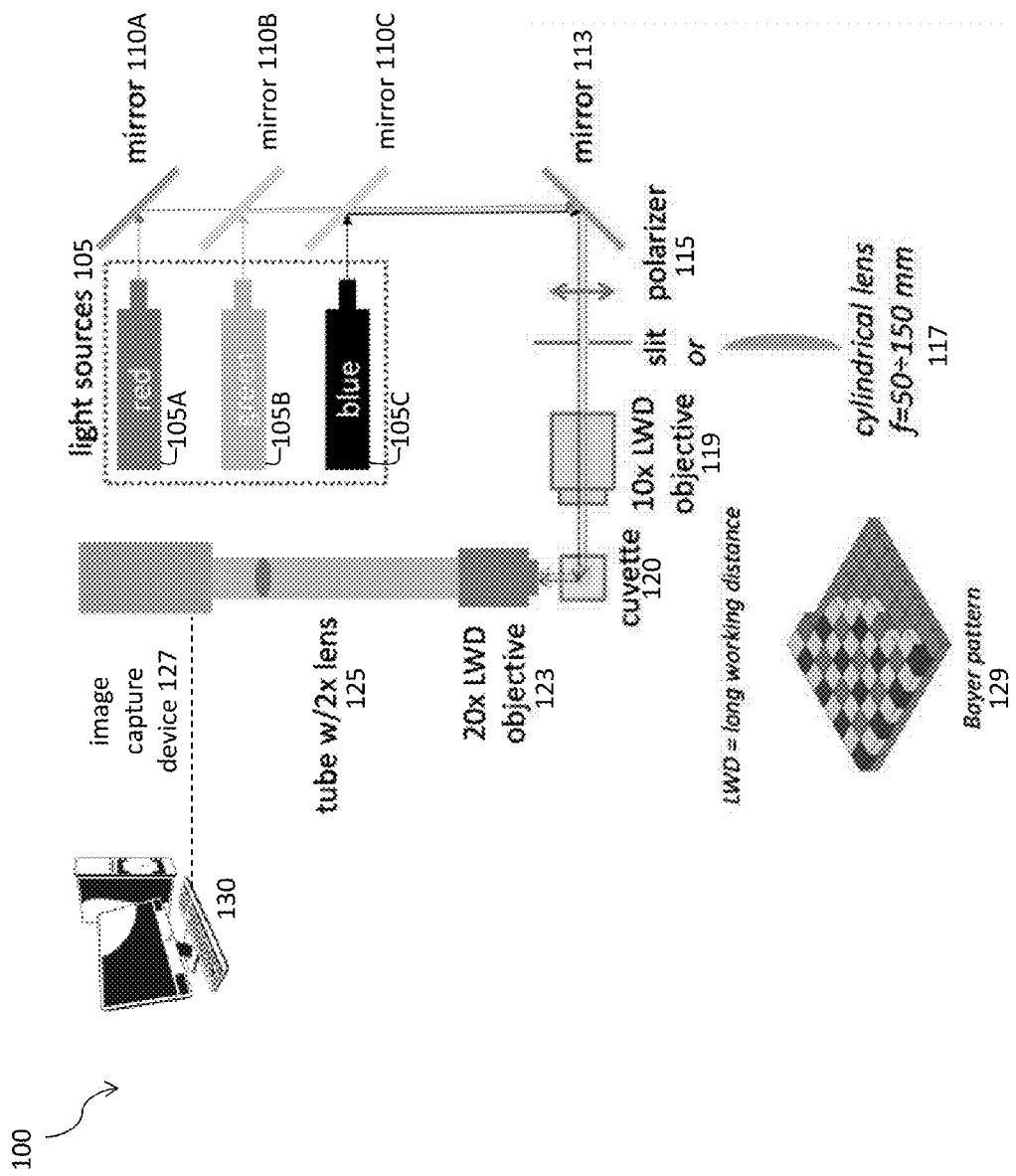
FIG. 1 illustrates a system for detecting and analyzing individual nanoparticles, in accordance with some example implementations.

Like labels are used to refer to same or similar items in the drawings.

DETAILED DESCRIPTION

The subject matter disclosed herein provides techniques for detecting, tracking, and analyzing individual nanoparticles of varying sizes in a liquid medium using multispectral analysis. In some implementations, individual nanoparticles can range in size from approximately 10 nanometers to approximately 1 micrometer. These techniques may illuminate nanoparticles suspended in a liquid sample and record the Brownian motion of individual nanoparticles. These recordings may be analyzed to determine a particle size distribution of the nanoparticles. The particle size distribution may be representative of a number of nanoparticles per unit volume of sample within a particular size bin.

FIG. 1 illustrates an exemplary system 100 for performing the techniques disclosed herein. Light source 105 may generate a plurality of light beams that illuminate a liquid sample of nanoparticles. Light source 105 may include one or more lasers, one or more light emitting diodes (LEDs), and the like in any combination thereof. In the implementation of FIG. 1, light source 105 may include three light sources 105A, 105B, and 105C, which output light at different wavelengths and at separately regulated output power levels. For example, light source 105A may output a light beam (e.g., at 650 nm) in the red spectral waveband of the visible electromagnetic spectrum; light source 105B may output a light beam (e.g., at 520 nm) in the green spectral waveband of the visible electromagnetic spectrum; and light source 105C may output a light beam (e.g., at 470 nm) in the blue spectral waveband of the visible electromagnetic spectrum. While three light sources are used in the implementation of FIG. 1, any number of light sources operating in any number of different wavebands can be employed including, for example, wavebands outside of the visible portion of the electromagnetic spectrum. In some implementations, for example, only a single tunable laser light source 105 may be used. In other implementations, one or two of light sources 105A, 105B, and 105C may be used.

The light beams output from light sources 105A, 105B, and 105C may be combined into one or more multi-color light planes (or sheets) which can illuminate a liquid sample of suspended nanoparticles. An optical assembly having various optical components may be used to combine these light beams. The optical components in the optical assembly may include, for example, at least one or more mirrors, beam combiners, slits, cylindrical lenses, long working distance objectives, and the like and in any combination thereof. In the implementation of FIG. 1, for example, mirrors 110A, 110B, and 110C, can reflect the light beams output from light sources 105A, 105B, and 105C, respectively, to mirror 113. Mirror 113 may combine the separate light beams into a single multi-color light sheet. The single multi-color light sheet may pass through one or more of slit 117 and long working distance objective 119 to illuminate a liquid sample of nanoparticles held in a sample container, such as cuvette 120. In some implementations, a cylindrical lens may be used instead of slit 117. In some implementations, the single multi-color light sheet may optionally pass through polarizer 115 before illuminating the liquid sample, as described below with respect to FIG. 2. Cuvette 120 and its liquid sample may be placed within a sample holder in order to control and measure the temperature of the liquid sample. The arrangement of optical components in the implementation of FIG. 1 may be associated with the use of a laser light source 105. Other arrangements of optical components may be used when different types of light sources 105 are used.

Nanoparticles suspended in the liquid sample may scatter the incident light from the multi-color light sheet. Because the liquid sample may have nanoparticles of different sizes, the magnitude of light scattered by these nanoparticles may vary. Long working distance objective 123 may collect the scattered light within a predetermined range of scattering angles. The numerical aperture of long working distance objective 123 may determine the angle of collected scattered light. The nanoparticles in the liquid sample may scatter light into an angle centered around an axis at approximately 90 degrees with respect to the direction of the incident multi-color light sheet. Long working distance objective 123 may collect light scattered within approximately ±10 degrees to approximately ±20 degrees around this center axis. In the implementation of FIG. 1, for example, long working distance objective 123 may collect light scattered at angles from about 75 degrees to 105 degrees, although other scattering angles and light collection configurations may be implemented as well.

The scattered light may propagate through tube and lens 125, and image capture device 127 may detect and record the scattered light. The volume of sample producing the scattered light may be on the order of 1 nanoliter (nL), for example. In the implementation of FIG. 1, image capture device 127 may be a video camera system (e.g., a digital video camera), although other types of image capture devices may be used. Image capture device 127 may simultaneously detect and record information provided by the scattered light in the same or substantially similar wavebands as the light beams output from light source 105. In some implementations, two separate devices may perform the detection and recording of information provided by the scattered light (e.g., by a separate detector and a separate recorder) instead of consolidating these functions into a single device as illustrated in the implementation of FIG. 1.

If light sources 105A, 105B, and 105C are red, green, and blue wavelength lasers, for example, image capture device 127 may be a color video camera having a detector that can separately detect each of the three wavelengths. For example, if light source 105A outputs a light beam at a particular wavelength (e.g., 650 nm) within the red spectral waveband, then image capture device 127 may be configured to detect light within the entirety of the red spectral waveband or a portion thereof. Similarly, if light source 105B outputs a light beam at a particular wavelength (e.g., 520 nm) in the green spectral waveband, then image capture device 127 may be configured to detect light within the entirety of the green spectral waveband or a portion thereof. Likewise, if light source 105C outputs a light beam at a particular wavelength (e.g., 470 nm) in the blue spectral waveband, then image capture device 127 may also be configured to detect light within the entirety of the blue spectral waveband or a portion thereof. In the example of FIG. 1, a Bayer pattern detector (or filter) 129 may be used at the photosensors' pixel array. In the case of Bayer filter pattern 129, it may be 50% green, 25% red, and 25% blue on a 2×2 pixel grid, and the two green pixels may be diagonally positioned, although other detector configurations may be used as well. Using a Bayer pattern filter allows image capture device 127 to separately detect and record the nanoparticle light scattering in each of the three separate wavelengths/colors without combining the Bayer pattern into RGB pixels (as combining the Bayer pattern into RGB pixels may lose the detection resolution provided by separately detecting the wavelengths/colors). In some implementations, image capture device 127 may include a 3-CCD video camera to detect data in different wavebands of light, although other types of detectors may be used as well. These different wavebands may correspond to the spectral bands of light output by light sources 105A, 105B, and 105C, although a single video camera having a plurality of detectors (for example, one for each laser source as in the Bayer pattern) may be implemented as well.

Image capture device 127 may record one or more movies based on the light scattered by the sample of nanoparticles. These movies may contain information representative of the Brownian motion of the nanoparticles. Individual nanoparticles may be seen as bright spots undergoing Brownian motion in these movies. Image capture device 127 may record these movies at least at 25 frames per second (fps). While a variety of movie lengths may be used, each movie is preferably 10 to 15 seconds long, as this length is generally adequate for statistically significant tracking and analysis of the Brownian motion of individual nanoparticles. For example, if image capture device 127 records movies at 30 frames per second, then the length of a single movie may be about 10 seconds to 15 seconds long (or 300 frames to 450 frames).

Image capture device 127 may record multiple movies for different aliquots of a given sample in order to ensure statistically robust results. These movies may be stored as raw data or raw patterns. For example, if image capture device 127 is a color video camera, then the movies may be stored in a raw Bayer pattern. These movies may be stored at image capture device 127 or remotely at computing device 130. Computing device 130 may have at least one processor that may be configured to analyze these raw patterns of video data to determine the concentration and size distribution of nanoparticles.

As described above, system 100 may optionally include a polarizer 115. Polarizer 115 may vertically polarize the multi-color light sheet relative to the scattering plane before it illuminates the liquid sample.

Figure 2:
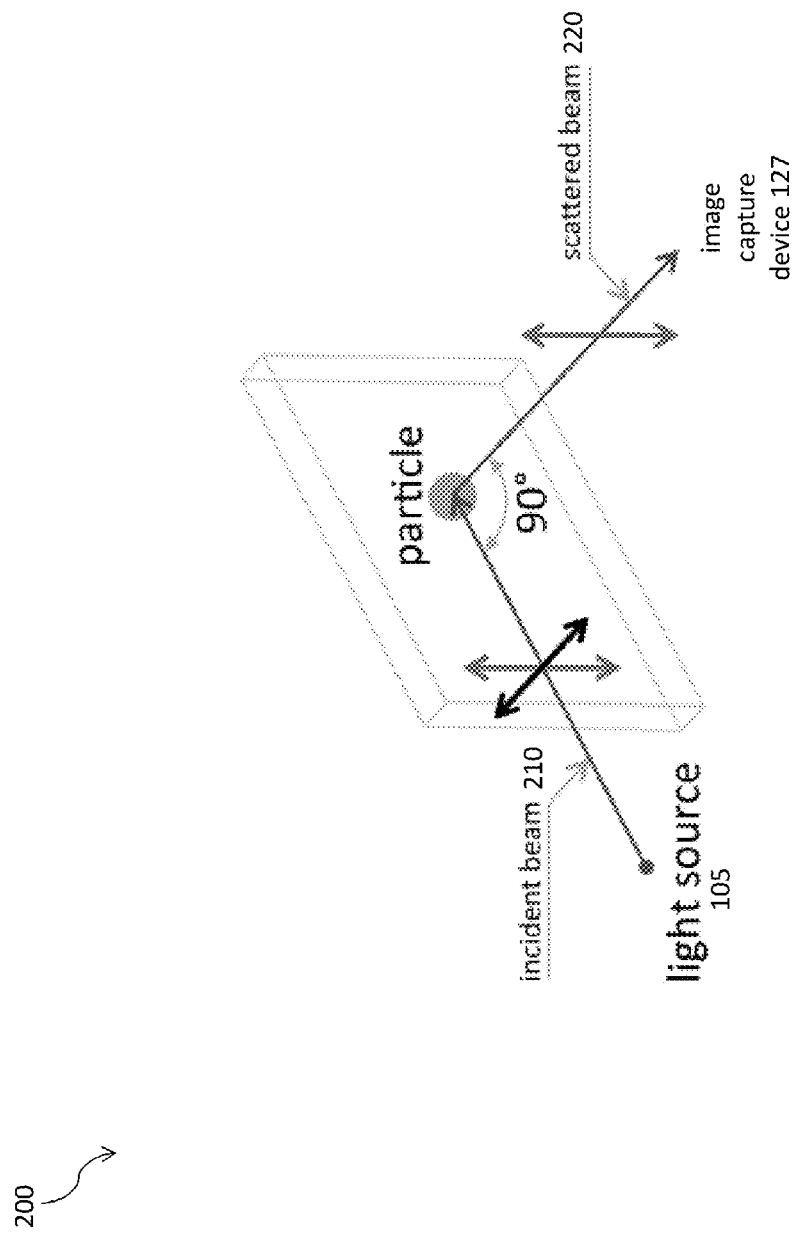
FIG. 2 illustrates the illumination of a liquid sample using linearly polarized light, in accordance with some example implementations.

Generally, the sensitivity of nanoparticle detection may depend on the intensity of scattered light. At the scattering angles described above, the contribution of vertically polarized light may be dominant, and the contribution of horizontally polarized light may be substantially negligible. FIG. 2 illustrates the illumination of a nanoparticle in the liquid sample using randomly polarized light beam 210. The horizontal component of the incident beam may heat the liquid sample of nanoparticles. This heating may adversely affect the detection of nanoparticles. Adding polarizer 115 to system 100 may eliminate this horizontal component of the incident beam and reduce the adverse impact on nanoparticle detection. Polarizer 115 may only allow the vertical component of incident beam 210 to strike the nanoparticle, which may not effect nanoparticle detection because the vertically polarized light 220 is the dominant component of scattered intensity at near normal angles.

The nanoparticles may also emit or be caused to emit radiation, such as fluorescence, for example, by virtue of their interaction with the incident light beams. Image capture device 127 may detect such radiation, for example fluorescence, in a similar manner as described above with respect to the detection of scattered light.

In some implementations, the subject matter disclosed herein may provide a system and method for eliminating problems associated with potential underexposure and overexposure of nanoparticles of different sizes. These problems may be resolved using a combination of multi-spectral sample illumination using different intensity illuminating beams in different spectral bands and simultaneous multi-spectral detection of light scattered by nanoparticles.

For example, the scattered intensity produced by small nanoparticles (i.e., less than about 100 to 200 nm) may be stronger in the blue spectral band than in the green and red spectral bands. In order to optimize the detection and analysis of small nanoparticles, a blue light source 105C operating at a relatively high output power (e.g., in the range from about 500 mW to 1000 mW, for example) may be used to illuminate the liquid sample. In a similar fashion, the detection and analysis of medium nanoparticles (between about 100-200 nm and 400-500 nm) may be optimized by illuminating the sample with a green light source 105B. The green light source 105B may operate at a lower output power than the blue light source (e.g., from about 50 mW to 200 mW, for example). The detection and analysis of large nanoparticles (i.e., larger than about 400-500 nm) may be optimized by illuminating the sample with a red light source that operates at a low output power (e.g., from about 20 to 100 mW, for example).

Computing device 130 may analyze all nanoparticles including the range of small, medium, and large nanoparticles from the same liquid sample simultaneously using image and/or video information recorded at the blue, green, and red colors, respectively. Because these size ranges may overlap with each other, the subject matter disclosed herein may enable the simultaneous determination of concentration and size distribution of nanoparticles over the entire range of nanoparticle sizes. In contrast, if the liquid sample is illuminated with a single monochromatic light beam at a constant power, then small nanoparticles that produce low intensity scattered light may be underexposed or undetected.

This adverse effect may lead to an underestimation of small nanoparticles. Likewise, large nanoparticles may produce high intensity scattered light and may be overexposed. This overexposure may introduce artifacts that can affect the tracking of the Brownian motion of these particles, the determination of the size of these particles, and impact the ability to detect small underexposed nanoparticles in the vicinity of large overexposed particles.

Figure 3:
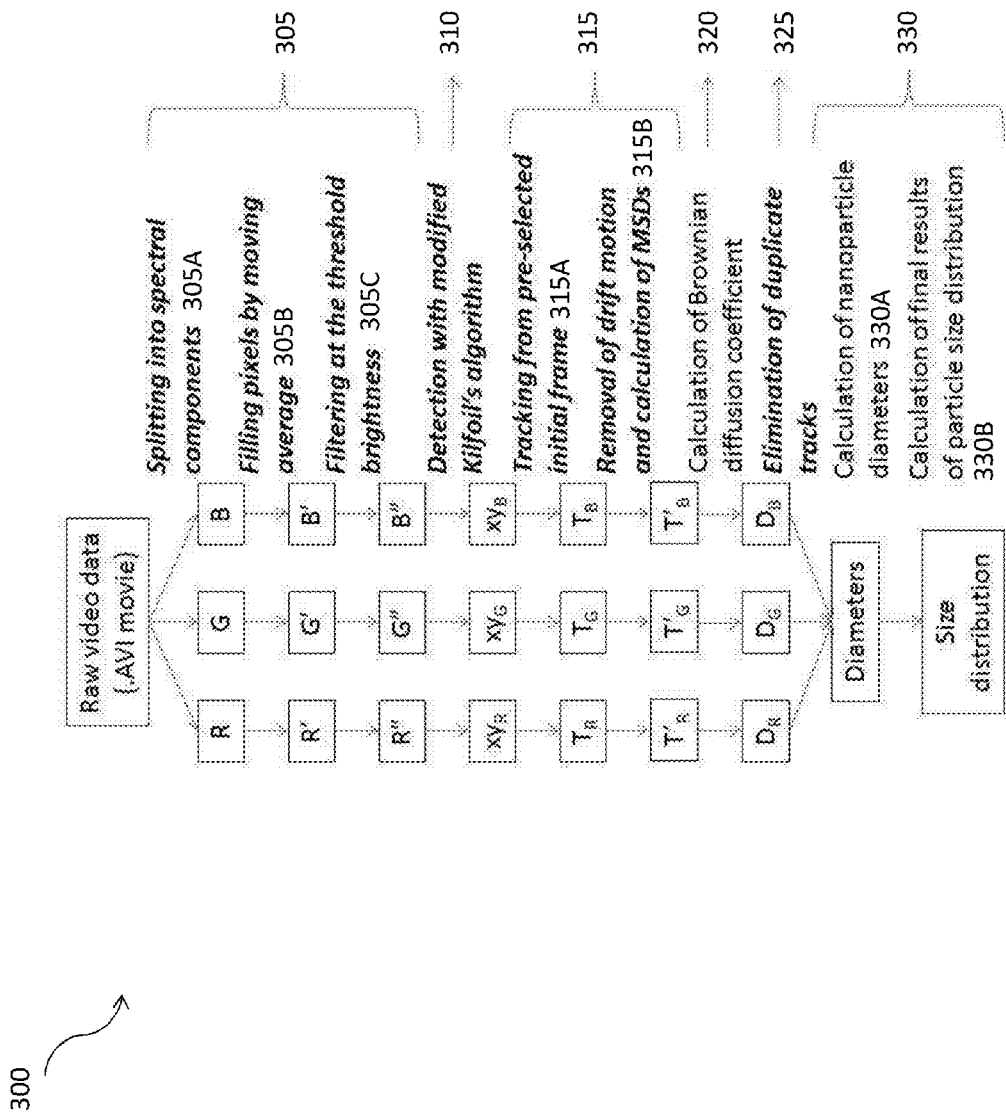
FIG. 3 illustrates a process for analyzing image data of nanoparticle motion, in accordance with some example implementations.

Computing device 130 may perform process 300, as illustrated in FIG. 3, to analyze data (e.g., image data, video data, and the like) from image capture device 127 and determine a particle size distribution of nanoparticles (i.e., the concentration of nanoparticles as a function of nanoparticle size) in the liquid sample. As described above with respect to FIG. 1, the video data may be representative of nanoparticle Brownian motion and may be recorded in a raw pixel pattern.

Computing device 130 may obtain the video data using a video recording and acquisition application program. This program may be configured to perform various operations relating to system 100. For example, this program can take temperature measurements of the liquid sample at predetermined intervals or on demand. Computing device 130 may use these temperature measurements to calculate nanoparticle diameters from the Brownian diffusion coefficients associated with the nanoparticles. The program may also set and read the output power of light sources 105A, 105B, and 105C and control the delivery of the liquid sample to cuvette 120. The program may include an input file having one or more data acquisition parameters. This input file may initiate a recording of a movie or a series of movies (for example, one or more images, a digital video, and the like) using image capture device 127. The data collected by the video recording and acquisition application program may be stored in a log file at image capture device 127 or computing device 130. Computing device 130 may use this log file to analyze the collected image and video data.

Process 300 may be divided into subprocesses 305, 310, 315, 320, 325, and 330. Each of these subprocesses is described below.

At subprocess 305, computing device 130 may process the video data collected from image capture device 127. At 305A, computing device 130 may split the video data collected from image capture device 127 into its spectral components. As described above with respect to FIG. 1, image capture device 127 may be a color camera having a Bayer filter pattern, for example. The color camera may record nanoparticle movement in a raw pattern mode using the Bayer filter. During subprocess 305A, computing device 130 may separately extract the red, green, and blue components (i.e., the grey-scale intensity or brightness of the pixels) from the video data for each frame of the movie. The symbols R, G, and B illustrated at 305A refer to the raw video data recorded in the red, green, and blue spectral wavebands, respectively.

At 305B, computing device 130 may fill in any missing pixels using a moving average. Because image capture device 127 may use a Bayer pattern filter to record the video data, each pixel may record only one of the red, green, and blue colors. For example, in a 2×2 pixel grid, only 50% of the pixels (i.e., 2 pixels) may be green. Computing device 130 may backfill the missing 2 pixels (i.e., the non-green pixels) with brightness values using a moving average value. This moving average value may, for example, have a running length of 4 pixels. The symbols R', G', and B' illustrated at 305B refer to the raw video data in the red, green, and blue wavebands, respectively, after the missing pixels in each waveband are filled in.

Computing device 130 may filter the video data generated from 305B using a threshold brightness value at 305C. Computing device 130 may determine a histogram of pixel brightness values for each frame of the movie and select one or more threshold brightness values from the histogram. Computing device 130 may compare each pixel's intensity value to this threshold brightness value. If, for example, a pixel's intensity value is less than the threshold value, then the computing device 130 may set the pixel intensity to zero in order to minimize the possible effects of noise (i.e., the background brightness) in the image. The symbols R", G", and B" illustrated at 305C refer to the resulting video data in the red, green, and blue wavebands, respectively after the filtering is completed.

Figure 4:
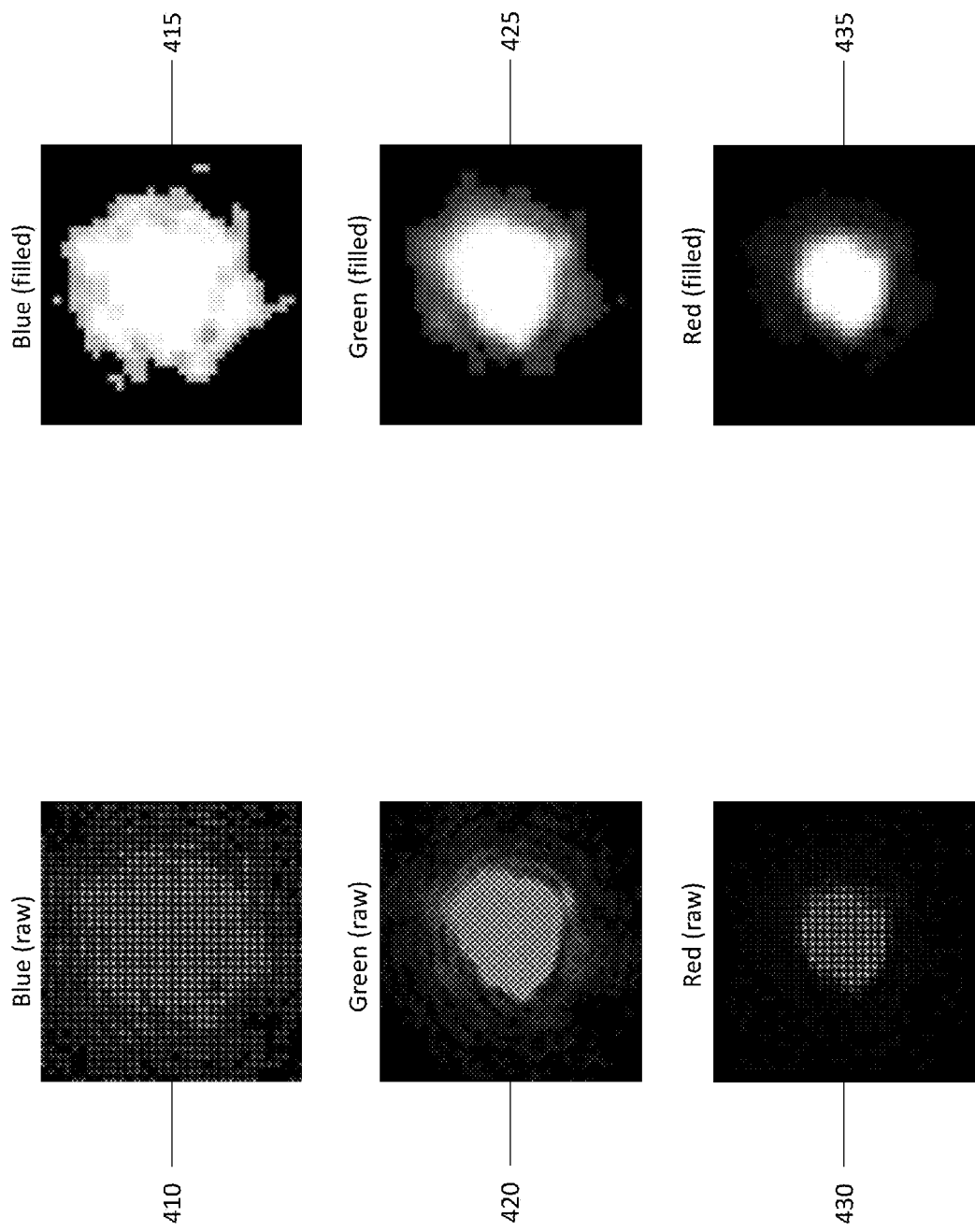
FIG. 4 is an image of a single nanoparticle in different spectral bands generated from a video camera having a Bayer pattern filter, in accordance with some example implementations.

FIG. 4 illustrates a series of images 410, 415, 420, 425, 430, and 435 of light scattered by a single nanoparticle in the red, green, and blue spectral bands. Computing device 130 may generate these images based on the operations performed at 305A, 305B, and 305C using a CCD video camera having a Bayer pattern filter. Images 410, 420, and 430 show raw unprocessed images of the nanoparticle in the blue, green, and red spectral bands, respectively. In these raw images, bright spots may correspond to pixels of the Bayer pattern that detect light within a given specific spectral band. Dark areas between bright spots may correspond to pixels from the two other spectral bands. Images 415, 425, and 435 show the nanoparticle after computing device 130 fills the dark pixels using a moving average. As evident from these images, the red band provides the best image of the nanoparticle in image 435 when the nanoparticle is large (800 nm in diameter in this example illustration).

Returning to FIG. 3, at subprocess 310, computing device 130 may identify and detect the presence of nanoparticles in the video data. The symbols $xy_R$, $xy_G$, and $xy_B$ illustrated at 310 refer to the x and y coordinates of the nanoparticles detected in each movie frame and in each spectral band. Nanoparticles may be displayed as bright features or blobs on the movie frames. Computing device 130 may detect the presence of blobs using a modified form of the "Particle Pretracking and Tracking, and 2D Feature Finding" algorithm developed by Maria L. Kilfoil (referred to as "Kilfoil's algorithm"). Computing device 130 may use Kilfoil's algorithm to find and track the motion of predetermined features in the video data for further analysis. Generally, nanoparticle features, referred to herein as blobs, tend to be circular and bright. Non-nanoparticle features associated with noise or other artifacts may be elliptical, extended in shape, and less intense or bright than a nanoparticle. Computing device 130 may use Kilfoil's algorithm in order to identify and locate the desired nanoparticle features on each frame and in each spectral waveband of the video data. Modifications to Kilfoil's algorithm may optimize the acceptance of blobs and the rejection of background noise or other false (non-nanoparticle) features in each waveband and in each frame of a movie. These modifications are described below and may be used in any combination and in any order.

In a first modification to Kilfoil's algorithm, computing device 130 may compute one or more of an intensity threshold value and a size threshold value for a nanoparticle. These parameters may assist with the differentiation of nanoparticle blobs from false features or background noise. Computing device 130 may compute one or more of these parameters in each spectral band and in each frame of a movie.

The intensity threshold may be determined on the basis of intensity values of all blobs that are present in a frame. The intensity value for a given nanoparticle blob or false feature may be calculated as the integrated intensity of all pixels under a mask that is convolved with a blob or feature. In these calculations a pixelated disk-shaped mask may have a predefined diameter (e.g., 20 pixels), and each pixel within the mask is assumed to have an intensity of value of 1.

The size threshold may be determined from the size values of all blobs and other features that are present in the frame. The size of a given blob or other feature may be calculated as the squared radius of a gyration of the blob or the feature.

Starting with a first frame of a movie, computing device 130 may apply the intensity and size threshold values described above to each frame of a movie and to each spectral component in order to differentiate nanoparticles (blobs) from noise or other false features. Computing device 130 may track nanoparticles over time in each spectral band starting from a pre-selected initial frame on a frame-by-frame basis. In some implementations, the initial frame may not be the first frame of the movie.

In a second modification to Kilfoil's algorithm, computing device 130 may adjust the manner in which the size threshold is applied. For example, when analyzing the blue and green spectral components of a movie, computing device 130 may apply the size threshold regardless of the brightness of the blobs in a frame. Computing device 130 may accept blobs that are smaller than the size threshold for subsequent tracking and analysis. Computing device 130 may reject blobs that are larger than the size threshold. In each frame, the size threshold may correspond, for example, to the average size of the blobs in the frame or the average blob size less a predetermined blob size. The predetermined blob size may correspond to the size of a disk-shaped mask (e.g., 20 pixels in diameter), for example. This modification may enhance the rejection of false features, especially in the blue waveband.

In a third modification to Kilfoil's algorithm, computing device 130 may adjust the manner in which the intensity threshold is applied. For example, when analyzing the red spectral component of a movie, computing device 130 may apply the intensity threshold regardless of blob size. Computing device 130 may accept blobs (i.e., accept them as nanoparticles) having an integrated intensity higher than the intensity threshold. Computing device 130 may reject blobs having an integrated intensity lower than the intensity threshold. For each frame, the intensity threshold may correspond to highest integrated intensity multiplied by a scalar factor (e.g., 0.1).

In a fourth modification to Kilfoil's algorithm, computing device 130 may remove ring-like artifacts which may be associated with individual blobs. These artifacts may appear when a blob in the sample appears out of focus and may lead to the false detection of a nanoparticle. To remove these artifacts, computing device 130 may determine the distance between neighboring blob features in each frame. If the distance is less than a predetermined value (e.g., a selected multiple of the size threshold for the frame), then computing device 130 may reject the blob from further analysis.

At subprocess 315, computing device 130 may track the movement of nanoparticles (during 315A) and remove any drift (non-Brownian motion) exhibited by the nanoparticles (during 315B). During the former, computing device 130 may separately track the Brownian motion of nanoparticles detected during subprocess 310. Computing device 130 may separately track nanoparticles over time on a frame-by-frame basis and in each spectral band. The tracking process may be based on various predetermined criteria including, for example, a maximum particle displacement between consecutive frames (e.g., 11 pixels), a minimum number of frames in a track (e.g., 5), and a maximum gap between frames in which the position of a nanoparticle is undetermined (e.g., 4). The track is considered valid if it satisfies some, if not all, of the predetermined criteria. The symbols $T_R$, $T_G$, and $T_B$ illustrated at 315A refer to the valid tracks of nanoparticles recorded in each spectral band. Tracking may begin at a pre-selected initial frame of the movie (e.g., frame 1) and continue through all subsequent frames until the end of the movie or until the end of the longest track is reached.

While the tracking process performed at 315A may be based on Kilfoil's algorithm, computing device 130 may employ various enhancements to improve the accuracy of this process. In a first aspect, computing device 130 may only track those nanoparticles which are detected on the pre-selected initial frame of the movie. This modification may prevent a nanoparticle from being counted multiple times and may be helpful in situations where a nanoparticle disappears after the initial frame (e.g., because its track is terminated) and then reappears in another frame during a movie. In addition, computing device 130 may ignore any "new" nanoparticles that are absent from the initial frame but appear in subsequent frames.

In another aspect, computing device 130 may repeat the tracking process multiple times using different pre-selected initial frames in order to improve the statistical robustness of the obtained results. For example, computing device 130 may repeat the tracking process described above five times for a given movie starting at frames 1, 11, 21, 31, and 41. By averaging the obtained data over these iterations, computing device 130 may obtain results that are more accurate than the results obtained from a single movie. In some implementations, this process may be extended and repeated for different aliquots of the liquid sample by acquiring and analyzing multiple movies, each movie corresponding to a different aliquot of the sample.

At 315B, computing device 130 may calculate the translational drift of nanoparticles within the liquid sample. Drift motion may arise, for example, when the illuminating light beam heats and causes convective motion in the liquid sample. Computing device 130 may calculate and remove this translational drift from the tracking results obtained at 315A. In order to do so, computing device 130 may compare simulations of Brownian motion of nanoparticles in the presence and absence of drift motion. The distance traveled by a given nanoparticle due to drift between a pair of video frames may be quantified as a fraction of the distance between the positions of the nanoparticle recorded in the frames. The following process describes the calculation of a drift correction factor.

First, computing device 130 may calculate the differences in the x and y positions between each pair of consecutive frames using position data from the two closest frames in which the particle is detected. This calculation may be performed from the start to the end of a track and may account for frames in which a particle is not detected.

In an example, a nanoparticle may be detected and tracked in frames 1, 3, 4, 7, 8, 10, and 11. Computing device 130 may calculate the differences in x and y positions of the nanoparticle between frames 1 and 3, between frames 3 and 4, between frames 4 and 7, between frames 7 and 8, between frames 8 and 10, and between frames 10 and 11. Because frame 1 is two frames away from frame 3, computing device 130 may divide the recorded difference by two in order to obtain the estimated difference per frame between frames 1 and 3. Similarly, because frame 3 is one frame away from frame 4, computing device 130 may take the difference in x and y positions between these frames and divide the difference by one. Computing device 130 may calculate the differences between the other pairs of frames in a similar manner.

Computing device 130 may add these calculated differences and divide this sum by one less than the number of frames within the track. This quotient may be multiplied by a correction factor, for example 0.45, to obtain the final estimate of the drift correction per frame.

Computing device 130 may calculate the final drift correction for any given frame by multiplying the drift correction per frame by the number of frames between a desired frame and the first frame in the track. Referring to the example above, computing device 130 may calculate the final value of the drift correction for frame 3 by multiplying the drift correction per frame by two because frame 3 is two frames away from the first frame (frame 1) in the track. Similarly, computing device 130 may calculate the final value of the drift correction for frame 4 by multiplying the drift correction per frame by three because frame 4 is three frames away from the first frame in the track. Computing device 130 may calculate the final value of the drift correction for the remaining frames in the track in a similar manner. The drift correction factor may be based on one or more Monte Carlo simulations of particle tracks associated with a combination of Brownian motion and drift motion. Other correction procedures and correction factors may be used to determine the drift correction factor.

Computing device 130 may obtain the corrected x and y positions of a nanoparticle in each frame by subtracting the final drift correction from the recorded x and y coordinates of the nanoparticle. The new corrected x and y positions may be attributable only to the Brownian motion of the nanoparticle. Computing device 130 may use the corrected x and y positions in each track in a movie to compute the value of the mean square displacement (MSD) of each nanoparticle at 315B. Occasionally, a sequence of movie frames may include a few frames for which the x and y positions of the nanoparticle are undetermined. Computing device 130 may account for the data in these "missing" frames to properly calculate the MSD values. The symbols $T'_R$, $T'_G$, and $T'_B$ illustrated at 315B refer to the valid tracks of nanoparticles recorded in each spectral band following correction for drift motion, which are used to calculate the MSD value for each nanoparticle.

At subprocess 320, computing device 130 may calculate the Brownian diffusion coefficient for each tracked nanoparticle using the MSD values calculated at 315B. Computing device 130 may calculate the Brownian coefficient for each nanoparticle in each frame and in each spectral band using known methods. In some implementations, computing device 130 may eliminate some tracks to avoid the generation of data of Brownian diffusion coefficients subject to unacceptably large errors. The symbols $D_R$, $D_G$, and $D_B$ illustrated at 320 refer to the Brownian diffusion coefficients of tracked nanoparticles in each spectral band.

At subprocess 325, computing device 130 may eliminate duplicate nanoparticles. Occasionally, the same nanoparticle can be detected and tracked in more than one spectral band. Computing device 130 may identify these duplicates based on a comparison of each nanoparticle's location in each spectral band and in each frame of a movie. If duplicate tracks for the same nanoparticle are identified in different spectral bands, computing device 130 may use the nanoparticle track that yields the smallest uncertainty in the calculation of the diffusion coefficient which is then used in the calculation of the nanoparticle size distribution. Computing device 130 may ignore any remaining duplicate tracks and associated Brownian diffusion coefficients.

During subprocess 330, computing device 130 may calculate one or more nanoparticle diameters (at 330A) and a size distribution of the nanoparticles in the liquid sample (at 330B).

With regard to the former, computing device 130 may calculate the hydrodynamic diameter of each detected and tracked nanoparticle using the Brownian diffusion coefficients obtained at 325. This calculation may be performed in accordance with known methods using, for example, the Einstein equation (often referred to also as Stokes-Einstein equation).

After calculating the diameter of all detected and tracked nanoparticles, computing device 130 may determine a particle size distribution of the nanoparticles in the liquid sample at 330B. The particle size distribution may represent the concentration of nanoparticles within each particular size bin (e.g., the number of nanoparticles per unit volume of sample within each size bin). Each size bin has a center corresponding to a different nanoparticle diameter. The bin widths may be as small as 1 nm, but different binning schemes may be used. Computing device 130 may display, for example, the particle size distribution and the concentration of nanoparticles associated with each size bin.

Figure 5:
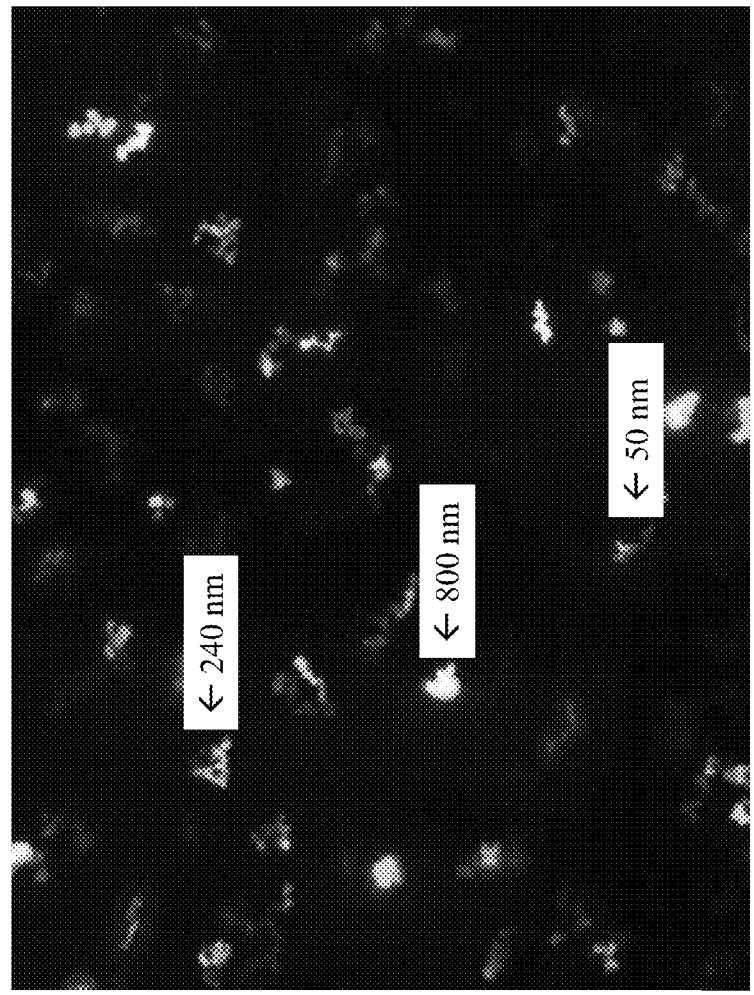
FIG. 5 is an image of polystyrene nanoparticles ranging in size between 50 nanometers and 800 nanometers in diameter suspended in water, in accordance with some example implementations.

FIG. 5 illustrates an image 500 of differently sized nanoparticles (a mix of standard polystyrene nanospheres with diameters of 50, 240 and 800 nm). The image represents a superposition of 300 video frames in the blue, green, and red spectral bands, acquired during a 10 second interval with nanoparticles suspended in water. The bright clusters or streaks represent trajectories (i.e., tracks) of individual nanoparticles over time. Computing device 130 may be configured to display FIG. 5 after performing process 325.

FIGS. 6A and 6B illustrate particle size distributions (PSDs) obtained from the validation experiments with two test samples consisting of mixtures of differently-sized nanoparticle size standards. The PSDs are depicted as density functions which may represent a concentration of particles of any given diameter per unit size interval of 1 nm. The integral of the density function over a given size range may yield the concentration of particles within that range. For example, the value of the density function at a diameter of 100 nm may represent a concentration of particles within a size bin of 1 nm width which ranges from 99.5 nm to 100.5 nm and has a center at 100 nm. The graphs in FIGS. 6A and 6B compare the PSDs obtained with the system disclosed herein and another unidentified system with a reference distribution.

FIGS. 6A and 6B show that the system disclosed herein provides highly accurate results for polydisperse samples as its PSD closely tracks the reference data points. In contrast, the PSD of the unidentified system greatly differs from the reference data points. For the sample presented in FIG. 6A (i.e., $N \sim d^{-1}$, where N is the nanoparticle concentration, and d is the nanoparticle diameter), the PSD of the unidentified system is significantly below the reference distribution. This behavior may indicate an underestimation of nanoparticle concentration across the entire range of nanoparticle sizes within the examined sample. The relative differences in concentration values between the unidentified system and the reference concentration values range from −81% to −34% at different diameters of the size standards, with an average difference of −61%. In contrast, the differences for the concentrations associated with the system disclosed herein and the reference concentration values are significantly smaller. These differences range from −42% to +9%, with an average difference of −15%.

For the sample presented in FIG. 6B (i.e., N~$d^{-3}$), the PSD of the unidentified system is significantly above the reference distribution. This behavior may indicate an overestimation of nanoparticle concentration. The relative differences between the unidentified system and the reference concentration range from +50% to +1,118%, with an average difference of +446%. In contrast, the differences for the concentrations associated with the system disclosed herein and the reference concentration values are significantly smaller ranging from 38% to +119%, with an average difference of +41%.

The results from FIGS. 6A and 6B demonstrate the presence of large errors in the unidentified system and also indicate that the bias in these measurements may vary largely from one sample to another. For example, the bias may be significantly negative for the N~$d^{-1}$ sample and may be highly positive for the N~$d^{-3}$ sample.

Without in any way limiting the scope, interpretation, or application of the claims appearing herein, a technical effect of one or more of the example implementations disclosed herein may include enhanced detection of nanoparticles.

The subject matter described herein may be embodied in systems, apparatus, methods, and/or articles depending on the desired configuration. For example, apparatuses and/or processes described herein can be implemented using one or more of the following: a processor executing program code, an application-specific integrated circuit (ASIC), a digital signal processor (DSP), an embedded processor, a field programmable gate array (FPGA), and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. These computer programs (also known as programs, software, software applications, applications, components, program code, or code) include machine instructions for a programmable processor, and may be implemented in a high-level procedural and/or object-oriented programming language, and/or in assembly/machine language. As used herein, the term "machine-readable medium" refers to any computer program product, computer-readable medium, computer-readable storage medium, apparatus and/or device (e.g., magnetic disks, optical disks, memory, Programmable Logic Devices (PLDs)) used to provide machine instructions and/or data to a programmable processor, including a machine-readable medium that receives machine instructions. Similarly, systems are also described herein that may include a processor and a memory coupled to the processor. The memory may include one or more programs that cause the processor to perform one or more of the operations described herein. For example, the control of the processes and operations disclosed herein may include computer code.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

Although a few variations have been described in detail above, other modifications or additions are possible. In particular, further features and/or variations may be provided in addition to those set forth herein. Moreover, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other implementations may be within the scope of the following claims. Furthermore, the specific values provided in the foregoing are merely examples and may vary in some implementations.

Although various aspects of the invention are set out in the claims, other aspects of the invention comprise other combinations of features from the described implementations with the features of the claims, and not solely the combinations explicitly set out in the claims.

What is claimed is:

1. A system comprising: a plurality of light sources configured to produce a plurality of light beams at different spectral wavebands; an optical assembly configured to combine the plurality of light beams into one or more multi-waveband incident light sheets, each multi-waveband incident light sheet illuminating one or more nanoparticles in a liquid sample; and one or more image detectors configured to detect, using a plurality of wavelengths, light scattered by one or more nanoparticles, the plurality of wavelengths corresponding to the different spectral wavebands of the plurality of light beams.

2. The system of claim 1 further comprising: a recording device configured to record a sequence of images obtained from the one or more image detectors in one or more movies.

3. The system of claim 2 further comprising: at least one processor configured to at least: detect and track a movement of the one or more nanoparticles based on at least two images from the sequence of images, the at least two images displaying a scattering of the one or more multi-waveband incident light sheets by the one or more nanoparticles; and determine a particle size distribution of the one or more nanoparticles from the one or more moves, the particle size distribution comprising one or more concentration values for one or more nanoparticle diameters.

4. The system of claim 3, wherein the detect and the track includes one or more of the following:
splitting the one or more movies into one or more separate spectral components to generate one or more spectral images and backfilling each spectral image;
eliminating one or more false features from the one or more movies, the eliminating based on one or more criteria including an intensity threshold or a size threshold;

tracking only a subset of the one or more nanoparticles that are present in one or more pre-selected starting frames of the one or more movies;
eliminating drift motion of the one or more nanoparticles; or
eliminating duplicate nanoparticle tracks from the one or more spectral components of the one or more movies.

5. The system of claim 1, wherein the one or more nanoparticles are moving.

6. The system of claim 1, wherein the one or more nanoparticles are not moving.

7. The system of claim 1, wherein each light beam is output at a separately adjustable power level and varying an intensity of one of the plurality of light beams relative to the other light beams based on the light scattered by one or more nanoparticles.

8. The system of claim 1, wherein the optical assembly includes one or more of a mirror, a beam combiner, a slit, a cylindrical lens, or a long working distance objective.

9. The system of claim 1, wherein the plurality of light beams are a part of a visible light spectrum.

10. The system of claim 1, wherein the plurality of light beams includes light beams having a blue spectral waveband, a green spectral waveband, and a red spectral waveband.

11. The system of claim 1, wherein the one or more image detectors comprises a Bayer pattern filter configured to separately filter the different spectral wavebands of the plurality of light beams into a plurality of separate images corresponding to the spectral wavebands of the plurality of light beams,
the system further comprises at least one processor configured to:
at least detect and track a movement of a first set of nanoparticles based solely on the plurality of images corresponding to a first spectral waveband; and
at least detect and track a movement of a second set of nanoparticles based solely on the plurality of images corresponding to a second spectral waveband.

12. The system of claim 1, wherein the one or more image detectors comprises a Bayer pattern filter configured to produce one or more Bayer pattern images having separate color pixels.

13. The system of claim 1, wherein the optical assembly further comprises a polarizer arranged between the plurality of light sources and the liquid sample, the polarizer configured to vertically polarize the plurality of light beams relative to a scattering plane in order to optimize illumination of the liquid sample relative to a thermal energy transferred to the liquid sample from the one or more multi-waveband incident light sheets.

14. The system of claim 1, wherein the one or more image detectors are further configured to detect, at the plurality of wavelengths, the light scattered by the one or more nanoparticles simultaneously.

15. The system of claim 1, wherein the one or more image detectors are further configured to at least detect light produced by fluorescence and/or other radiation emitted by the one or more nanoparticles.

16. The system of claim 1, wherein the one or more image detectors comprises a filter configured to separately detect the different spectral wavebands of the plurality of light beams into a plurality of separate images corresponding to the spectral wavebands of the plurality of light beams.

17. A method comprising: producing a plurality of light beams at different spectral wavebands; combining the plurality of light beams into one or more multi-waveband incident light sheets, each multi-waveband incident light sheet illuminating one or more nanoparticles in a liquid sample; and detecting, using a plurality of wavelengths, light scattered by one or more nanoparticles, the plurality of wavelengths corresponding to the different spectral wavebands of the plurality of light beams.

18. The method of claim 17, wherein the producing is performed by a plurality of light sources, wherein the combining is performed by an optical assembly that includes one or more of a mirror, a beam combiner, a slit, a cylindrical lens, or a long working distance objective, and wherein the detecting is performed by one or more image detectors.

19. The method of claim 17 further comprising: recording a sequence of images obtained from the detecting in one or more movies.

20. The method of claim 19 further comprising: detecting and tracking a movement of the one or more nanoparticles based on at least two images from the sequence of images, the at least two images displaying a scattering of the one or more multi-waveband incident light sheets by the one or more nanoparticles; and determining a particle size distribution of the one or more nanoparticles from the one or more movies, the particle size distribution comprising one or more concentration values for one or more nanoparticle diameters.

21. The method of claim 20, wherein the detecting and the tracking includes one or more of the following:
splitting the one or more movies into one or more separate spectral components to generate one or more spectral images and backfilling each spectral image;
eliminating one or more false features from the one or more movies, the eliminating based on one or more criteria including an intensity threshold or a size threshold;
tracking only a subset of the one or more nanoparticles that are present in one or more pre-selected starting frames of the one or more movies;
eliminating drift motion of the one or more nanoparticles; or
eliminating duplicate nanoparticle tracks from the one or more spectral components of the one or more movies.

22. The method of claim 17, wherein the one or more nanoparticles are moving.

23. The method of claim 17, wherein the one or more nanoparticles are not moving.

24. The method of claim 17, wherein each light beam is output at a separately adjustable power level and adjusting an intensity of one of the plurality of light beams relative to the other light beams based on the light scattered by one or more nanoparticles.

25. The method of claim 17, wherein the plurality of light beams are a part of a visible light spectrum.

26. The method of claim 17, wherein the plurality of light beams includes light beams having a blue spectral waveband, a green spectral waveband, and a red spectral waveband.

27. The method of claim 17, wherein the detecting comprises separately filtering, using a Bayer pattern filter, the different spectral wavebands of the plurality of light beams into a plurality of separate images corresponding to the spectral wavebands of the plurality of light beams; the method further comprises:
detecting and tracking a movement of a first set of nanoparticles based solely on the plurality of images corresponding to a first spectral waveband; and
detecting and tracking a movement of a second set of nanoparticles based solely on the plurality of images corresponding to a second spectral waveband.

28. The method of claim 17, wherein the detecting comprises producing, using a Bayer pattern filter, one or more Bayer pattern images having separate color pixels.

29. The method of claim 17 further comprising: vertically polarizing the plurality of light beams relative to a scattering plane in order to optimize illumination of the liquid sample relative to a thermal energy transferred to the liquid sample from the one or more multi-waveband incident light sheets.

30. The method of claim 17, wherein the detecting further comprises detecting, at the plurality of wavelengths, the light scattered by the one or more nanoparticles simultaneously.

31. The method of claim 17, wherein the detecting further comprises detecting at least light produced by fluorescence and/or other radiation emitted by the one or more nanoparticles.

32. The method of claim 17, wherein the detecting comprises separately filtering the different spectral wavebands of the plurality of light beams into a plurality of separate images corresponding to the spectral wavebands of the plurality of light beams.

* * * * *